United States Patent
Zheng et al.

(10) Patent No.: US 12,279,781 B2
(45) Date of Patent: Apr. 22, 2025

(54) 2D-IMAGE GUIDED ROBOTIC DISTAL LOCKING SYSTEM

(71) Applicant: Tsinghua University, Beijing (CN)

(72) Inventors: Gangtie Zheng, Beijing (CN); Shijie Zhu, Beijing (CN); Zhe Zhao, Beijing (CN); Yongwei Pan, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 479 days.

(21) Appl. No.: 17/237,397

(22) Filed: Apr. 22, 2021

(65) Prior Publication Data

US 2021/0259711 A1   Aug. 26, 2021

Related U.S. Application Data

(63) Continuation-in-part of application No. 16/875,930, filed on May 15, 2020.

(30) Foreign Application Priority Data

Oct. 30, 2019  (CN) .......................... 201911045998.6
Feb. 8, 2021   (CN) .......................... 202110172614.8

(51) Int. Cl.
*A61B 17/17*  (2006.01)
*A61B 17/72*  (2006.01)
(Continued)

(52) U.S. Cl.
CPC ...... *A61B 17/1703* (2013.01); *A61B 17/7233* (2013.01); *A61B 34/30* (2016.02); *A61B 2017/0092* (2013.01)

(58) Field of Classification Search
CPC ...... A61B 2017/0092; A61B 2090/064; A61B 2090/376; A61B 2090/3966; A61B 34/37;
(Continued)

(56) References Cited

U.S. PATENT DOCUMENTS 7,008,373 B2   3/2006  Stoianovici et al.
8,394,114 B2   3/2013  Schaller et al.
(Continued)

FOREIGN PATENT DOCUMENTS

CN    1424673    6/2003
CN   101327148  12/2008
(Continued)

OTHER PUBLICATIONS

Patriciu, Alexandru et al. "Motion-Based Robotic Instrument Targeting Under C-Arm Fluoroscopy, Medical Image Computing and Computer-Assisted Intervention", Oct. 11-14, 2000, Pittsburgh, PA, Lecture Notes in Computer Science, Springer-Verlag, vol. 1935, pp. 988-998.
(Continued)

*Primary Examiner* — Christopher L Cook
(74) *Attorney, Agent, or Firm* — LOZA & LOZA, LLP; Michael F. Fedrick

(57) ABSTRACT

A 2D image-guided surgical robot system for distal locking operations includes surgical image acquisition equipment, a robot arm, a robot end effector attached to the robot arm, and a remote operation workstation. To perform a distal locking operation, the position of the image acquisition device is adjusted to obtain a round outline of a lockhole in the image. A distortion correction is performed. The position of the target lockhole is assigned by a user through the GUI of the remote operation workstation, and the remote operation workstation calculates a robot motion quantity using image feedback control law and moves the robot accordingly. The "image-and-move" procedure is repeated several times until the drill guide is accurately aligned to the lockhole, then the distal locking operation is accomplished by first drilling a guide hole using a guide wire through the drill guide, and then screwing a locking screw through the guide hole.

8 Claims, 9 Drawing Sheets

(51) Int. Cl.
*A61B 34/30* (2016.01)
*A61B 17/00* (2006.01)

(58) Field of Classification Search
CPC ............ A61B 17/1703; A61B 17/1725; A61B 17/7233; A61B 2034/104; A61B 2034/107; A61B 2034/2059; A61B 2034/2065; A61B 34/10; A61B 34/20; A61B 34/25; A61B 34/30; A61B 34/32; A61B 34/35; A61B 34/74; A61B 90/11; A61B 90/36; G06T 5/006; G06T 2207/10116; G06T 2207/30008; G06T 7/70; G06T 7/73
See application file for complete search history.

(56) References Cited

U.S. PATENT DOCUMENTS

| | | | |
|---|---|---|---|
| 8,992,580 B2 | 3/2015 | Bar et al. | |
| 9,498,231 B2 | 11/2016 | Haider et al. | |
| 9,872,733 B2 | 1/2018 | Shoham et al. | |
| 9,974,613 B2 | 5/2018 | Kang et al. | |
| 10,028,788 B2 | 7/2018 | Kang | |
| 2013/0073091 A1 | 3/2013 | Setsuda | |
| 2015/0085979 A1* | 3/2015 | Zheng | G06T 5/006 378/207 |
| 2015/0112344 A1* | 4/2015 | Shoham | A61B 34/70 606/64 |
| 2017/0042622 A1 | 2/2017 | Yang et al. | |
| 2018/0236270 A1* | 8/2018 | Hananel | A61N 7/00 |
| 2020/0170723 A1* | 6/2020 | Crawford | A61B 34/10 |
| 2020/0352659 A1 | 11/2020 | Zastrozna | |
| 2020/0360092 A1* | 11/2020 | Deng | A61B 34/32 |

FOREIGN PATENT DOCUMENTS

| | | |
|---|---|---|
| CN | 105395240 | 3/2016 |
| CN | 108392271 | 8/2018 |
| CN | 108601669 | 9/2018 |
| CN | 108938090 | 12/2018 |
| CN | 110123456 | 8/2019 |
| CN | 110141363 | 8/2019 |
| CN | 110197461 | 9/2019 |
| CN | 110236674 | 9/2019 |
| CN | 209392096 | 9/2019 |
| CN | 110325141 | 10/2019 |
| CN | 110709026 | 1/2020 |
| CN | 111297479 | 6/2020 |
| CN | 112006777 | 12/2020 |
| CN | 112869856 | 6/2021 |
| WO | 2019139841 | 7/2019 |

OTHER PUBLICATIONS

Lefranc, M. et al. "Evaluation of the ROSA Spine robot for minimally invasive surgical procedures", Expert Review of Medical Devices, vol. 13, No. 10, Oct. 2016, pp. 899-906.

Khan, A. et al. "Next-Generation Robotic Spine Surgery: First Report on Feasibility, Safety, and Learning Curve," Operative neurosurgery (Hagerstown, Md.), 2019, vol. 17, No. 1, pp. 61-69.

François Chaumette, S. Hutchinson, Visual servo control, Part I: Basic approaches, IEEE Robotics and Automation Magazine, Institute of Electrical and Electronics Engineers, 2006, 13(4):82-90.

* cited by examiner

2D-IMAGE GUIDED ROBOTIC DISTAL LOCKING SYSTEM

CROSS-REFERENCE TO RELATED APPLICATIONS

The present application is a continuation-in-part of U.S. patent application Ser. No. 16/875,930, filed on May 15, 2020, which claims the benefit of priority under 35 U.S.C. § 119 from Chinese Patent Application No. 201911045889.6, filed Oct. 30, 2019. The present application also claims the benefit of priority under 35 U.S.C. § 119 from Chinese Patent Application No. 202110172614.8, filed Feb. 8, 2021. The disclosures of the foregoing applications are incorporated herein by reference in their entirety.

INTRODUCTION/BACKGROUND

Intramedullary nailing is the gold standard for minimally invasive treatment of bone fracture, due to its high union rate and low complication rate. However, the surgical operation of intramedullary nailing, especially the distal locking procedure, is challenging for the surgeon. After the intramedullary nail is inserted into the bone shaft, a locking procedure is performed, i.e., to fixed the intramedullary nail to the bone by drilling several screws through the lockholes on the intramedullary nail. The lockholes locate at both ends of the intramedullary nail. Locking of the proximal lockholes (the ones close to the insertion point of the intramedullary nail) can be easily performed by attaching a drill guide to the proximal end of the intramedullary nail through the incision. While for the distal lockholes, due to the deformation of the intramedullary nail, the locking procedure must be performed with the help of X-ray images. Even though the surgeon can look through flesh and bone with an X-ray machine, drilling a guide hole through the lockhole whose diameter is usually below 5 millimeters is still a difficult operation. As a result, the X-ray exposure needed to accomplish a distal locking operation can be excessive, which is harmful for both the surgeon and the patient.

For an easier operation and less X-ray exposure, many computer-assisted techniques have been developed for distal locking. One of these solutions is based on optical navigation (see, Westphal R., Winkelbach S., Wahl F., et al., Robot-assisted long bone fracture reduction. International Journal of Robotics Research, 2009, 28(10):1259-1278). However, optical trackers need to be mounted on the patient, which can result in extra injuries. Other solutions are based on an electromagnetic navigation system, which needs a customized intramedullary nail with a built-in electromagnetic tracker and has a high requirement on the electromagnetic environment of the surgical room (see, Ioannis Stathopoulos, Panagiotis Karampinas, Dimitrios-Stergios Evangelopoulos., et al., Radiation-free distal locking of intramedullary nails: Evaluation of a new electromagnetic computer-assisted guidance system, Injury, 2013, 44(6):872-875).

An image-guided method using the visual servo technique is also a potential solution for distal locking. In recent years, visual servo technology has been receiving more attention in the field of robotics. In visual servo methods, motion and position information for the target and robot are obtained through images acquired by visual sensors. Such methods can be used in real time for robot motion control to guide a robot to complete a specific task, as discussed in Chaumette, et al. (Francois Chaumette and Seth Hutchinson, Visual servo control Part I: Basic approaches, IEEE Robotics & Automation Magazine, December 2006, pages 82-90). In the visual servo framework, a closed-loop control based on image feedback is used and the positioning accuracy of the robots is higher than that of open-loop control systems. On the other hand, with the development of digital image processing technology, the requirement of optical/electromagnetic trackers mounted on the target is becoming lower.

SUMMARY

The purpose of the proposed invention is to overcome the deficiencies of the prior technologies and provide a robot system for distal locking and a visual servo-based control method for distal locking. The proposed method only relies on C-arm X-ray machines commonly used in the operation room for closed-loop control, eliminating any optical/electromagnetic trackers.

Figure 1:
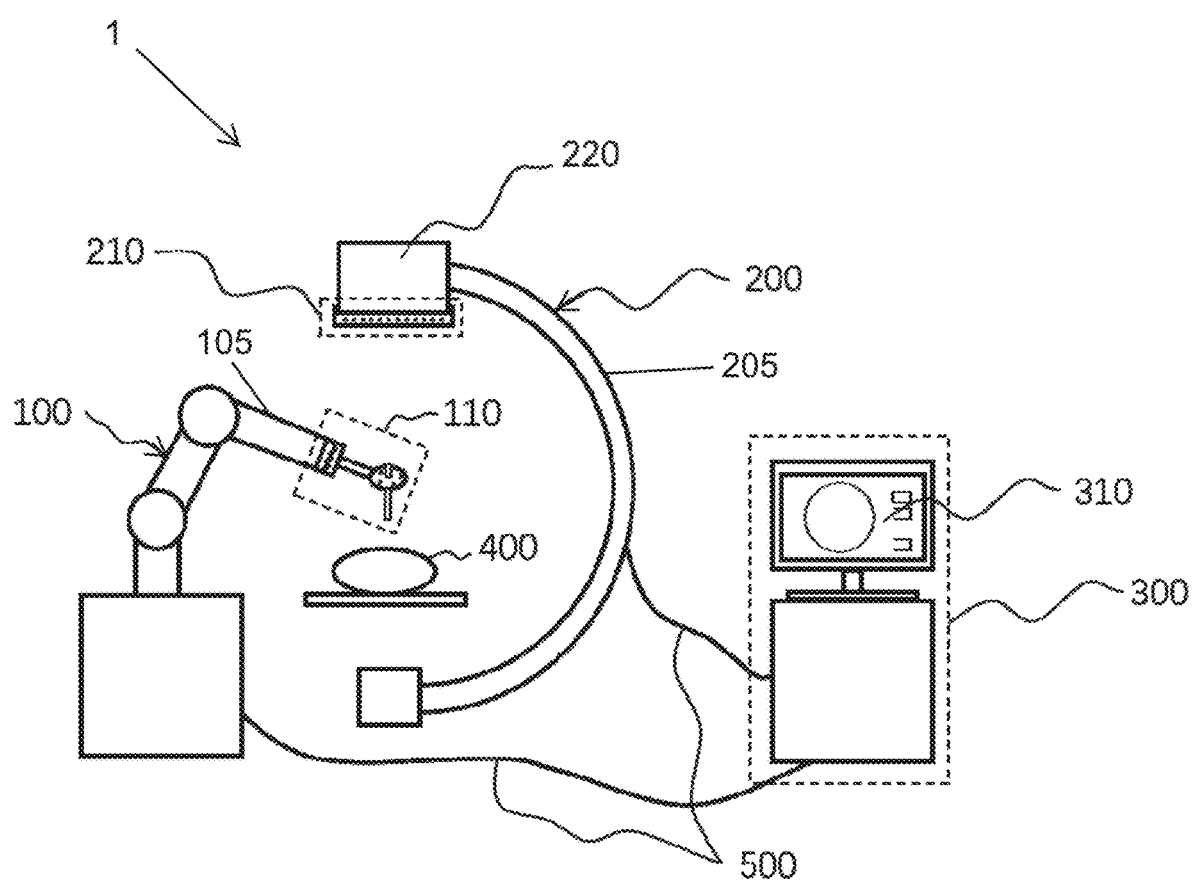
FIG. 1 is drawing of the hardware configuration of the present system.

The reference numbers in the figures have the following meanings:

| Component | Subcomponent | Reference Number |
|---|---|---|
| surgical robot system | | 1 |
| surgical robot | | 100 |
| end effector | | 110 |
| robot arm | | 105 |
| connector | | 111 |
| connector arm | | 112 |
| | connector arm proximal end | 112a |
| | connector arm distal end | 112b |
| drill guide | | 113 |
| beads | | 114 |
| | smaller diameter beads | a, b, c, d |
| | larger diameter beads | A, B, C, D |
| | smaller diameter circle | 115 |
| | larger diameter circle | 116 |
| | perpendicular axis line | 117 |
| registration device portion | | 130 |
| | proximal end | 131 |
| | distal end | 132 |

| Component | Subcomponent | Reference Number |
|---|---|---|
| | upper surface | 133 |
| | lower surface | 134 |
| | first plane | 135 |
| | second plane | 136 |
| | inner portion | 141 |
| | outer portion | 142 |
| | medial connecting wall | 145 |
| | right side wall portion | 146 |
| | left side wall portion | 147 |
| image acquisition device | | 200 |
| | C-arm of X-ray machine | 205 |
| | distortion correction device | 210 |
| | image intensifier of the image acquisition device | 220 |
| | plane plate | 221 |
| | grid dots | 212 |
| | patient | 400 |
| | data cable | 500 |

DETAILED DESCRIPTION

Definitions

As used herein, the following terms and variations thereof have the meanings given below, unless a different meaning is clearly intended by the context in which such term is used.

"2D" refers to two-dimensional areas, images, or other representations of two-dimensional areas. Images on a computer monitor are two-dimensional. "3D" refers to three-dimensional spaces or to representations of three-dimensional spaces.

"Array" and "grid" refer to an arrangement of lines, dots, or other forms in an ordered two-dimensional pattern, typically an arrangement in perpendicular rows.

"Bead" refers to a relatively small, typically rounded piece of material. The beads used in the present registration device are opaque to X-rays.

"Drill guide" refers to a hollow, usually cylindrical component that restricts the position and direction of a drill bit, i.e. the cutting portion of a drill.

"Image intensifier" refers to a component of an X-ray imaging system which intercepts x-ray photons and converts them into visible light photons and (b) amplifies or intensifies this light signal. Within an image intensifier, the input phosphor converts the x-ray photons to light photons, which are then converted to photoelectrons within the photocathode. The electrons are accelerated and focused by a series of electrodes striking the output phosphor, which converts the accelerated electrons into light photons that may be captured by various imaging devices.

"Image registration" refers to the process of transforming different sets of data into one coordinate system.

"Intermedullary" means within a medulla of a bone, such as within the marrow cavity of a bone. An "intermedullary rod" or "intermedullary nail" refers to a rigid, usually metal rod which can be inserted into the intermedullary cavity of a bone in order to stabilize and support the bone, for example a thigh, shin, hip, or upper arm bone.

"Normalized distance" refers to a ratio of the distance between (1) a first endpoint on a line and the crossing point with another line, and (2) the distance between the first endpoint to the other endpoint of the line.

The terms "above," "below," "between," and other terms of relative position or orientation as used herein refer to a relative position of one layer with respect to other layers. As such, one layer deposited or disposed above or below another layer may be directly in contact with the other layer or may have one or more intervening layers, unless described otherwise herein.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise. Ranges which are described as being "between" two values include the indicated values.

Surgical Robots

The present invention provides a 2D image-guided surgical robot system for distal locking and an image feedback control method, which overcomes the deficiencies of prior technologies with respect to their high hardware requirements, complicated workflow, and risk of iatrogenic injuries. The present image feedback control method only relies on 2D intraoperative X-ray images, so that the use of C-arm X-ray machines commonly used in operating rooms is sufficient to perform the present method, eliminating the use of extra optical\electromagnetic markers. X-ray images from only one direction are needed to perform surgery in the present method, while in prior art manual surgeries images collected from two directions are generally necessary for a surgeon to determine an entry point and drilling direction. This difference, together with the precise motion which robots are capable of, helps to greatly reduce the amount of radiation that patients and medical personnel are exposed to during bone surgeries, such as surgeries involving intramedullary nailing.

In one embodiment, the present system comprises a robot arm with a customized end-effector for distal locking, a surgical image acquisition device, an X-ray image distortion correction device, a remote operation workstation with a GUI for the doctors to interact with the system, and control software running on the workstation. The robot arm preferably has at least three translational degrees of freedom, or at least two rotational degrees of freedom. The remote operation workstation is connected to the surgical image acquisition system and the robot arm with data cables and is used to process the surgical images, mark the lockhole of the intramedullary nail, and control the motion of the robot arm. The surgical image acquisition device can provide intraoperative 2D X-ray images, including the commonly used C-arm X-ray machines.

FIG. 1 illustrates an embodiment of the present surgical robot system 1, which can include a robot arm 100, an end-effector 110, image acquisition device (C-arm X-ray machine) 200, image intensifier of the image acquisition device 220, distortion correction device 210, remote workstation 300, graphical user interface 310, and a data cable 500. The position of a subject 400 on which the present surgical robot 100 can be used is also shown. The remote operation workstation 300 can be connected to the surgical image acquisition system 200 and the robot arm 105 with data cables 500, and can be used to process surgical images, mark the locking hole of the intramedullary nail, and control the motion of the robot arm, for example. The surgical image acquisition device 200 provides intraoperative 2D X-ray images, and can be a G-arm or C-arm X-ray machine.

Figure 9:
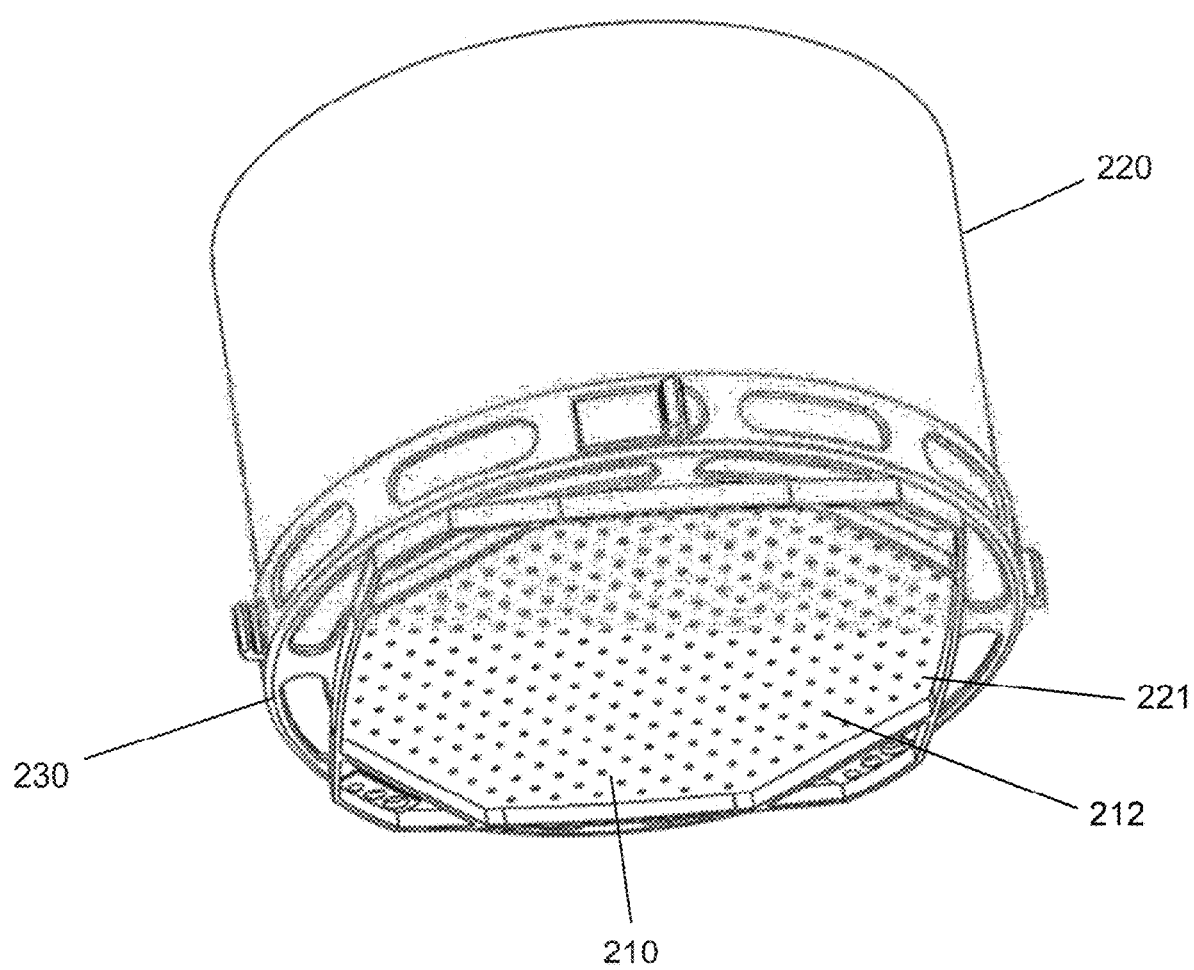
FIG. 9 is a perspective view of an X-ray image distortion correction device.

FIG. 9 is an illustration of an X-ray image distortion correction device 210 that can be used with the present surgical robot system 1. In this embodiment, a plane plate 221 is made from X-ray transparent material on which an array of beads 212 is embedded or otherwise attached or adhered to the plate 221. The beads 212 are opaque to X-rays, such as metal beads. The configuration of the metal bead array is predefined, and can be in the form of a grid as shown in FIG. 9. For example, as in the embodiment of FIG. 9, the metal beads are repeatedly arranged with a constant distance in two perpendicular directions. The image distortion correction device 210 is preferably reversibly secured to a distal end of the image intensifier 220, with the proximal end being attached to or integrally part of the remainder of image acquisition device 200. To perform X-ray image distortion correction, the X-ray image distortion correction device 210 is attached to the image intensifier 220 of the surgical image acquisition device and an X-ray image is then acquired. The X-ray image distortion correction device 210 should cover the field-of-view of the image intensifier so that the acquired X-ray image is filled with images of the metal beads. The mounting orientation of the X-ray image distortion correction device should not be restricted.

Figure 4:
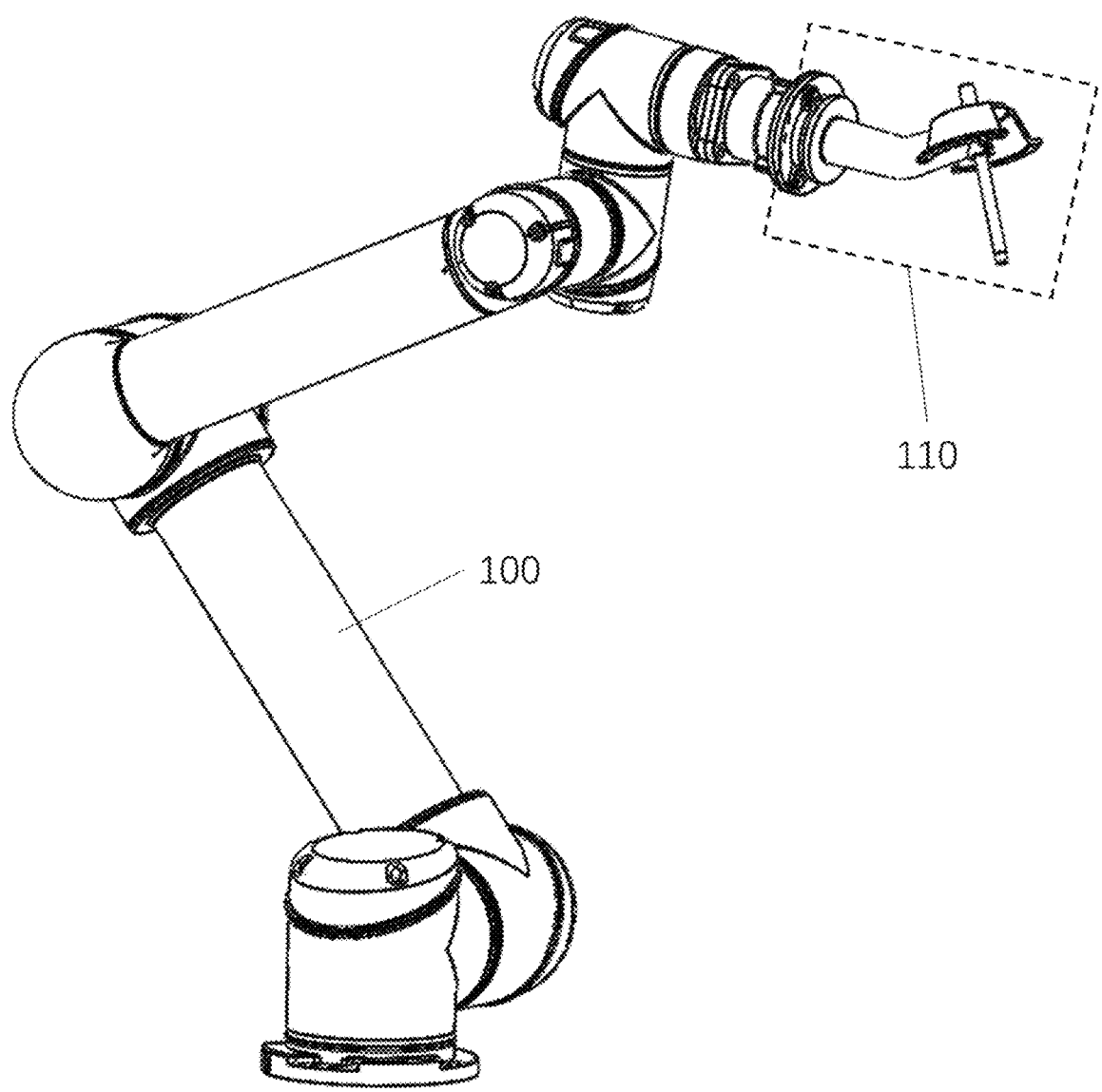
FIG. 4 is a perspective view of a robot arm with an end-effector.
Figure 5:
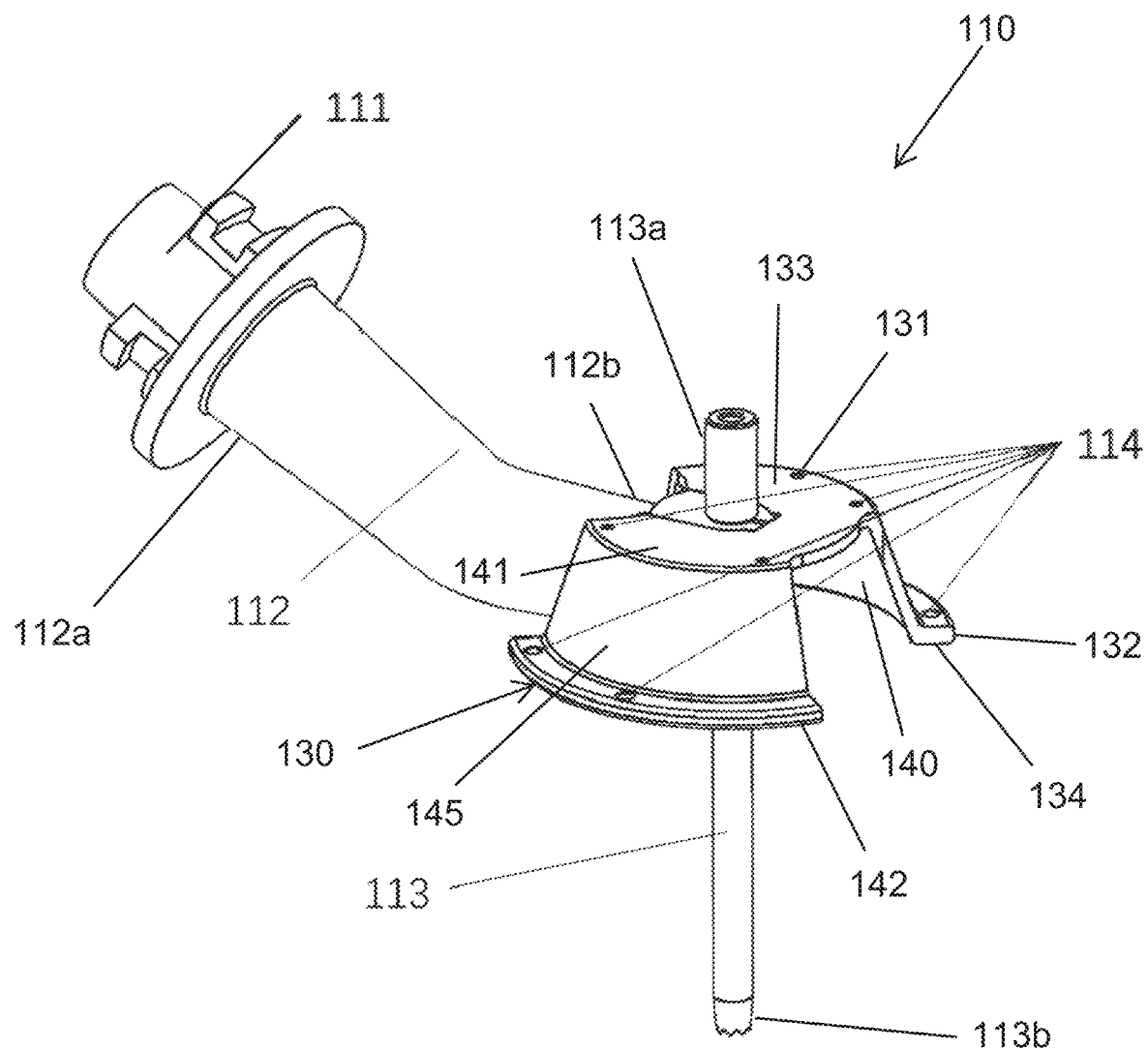
FIG. 5 is a perspective view of the end-effector of FIG. 4.

FIG. 4 illustrates a robot arm 100 with an end-effector 110 which can be used for distal locking of an intermedullary nail according to the present invention. FIG. 5 illustrates the end-effector in more detail. In this embodiment, the end effector 110 comprises a connector arm 112 having a connector 111 at its proximal end 112*a* for reversibly securing the end effector 110 to a robot arm 105. At the distal end 112*b* of the connector arm 112 is a drill guide 113 made from an X-ray transparent material which is held by the connector arm 112. The distal end 112*b* of the connector arm 112 also includes a registration device 130 having a base 140 made from an X-ray transparent material but embedded with beads that are opaque to X-rays.

Figure 7:
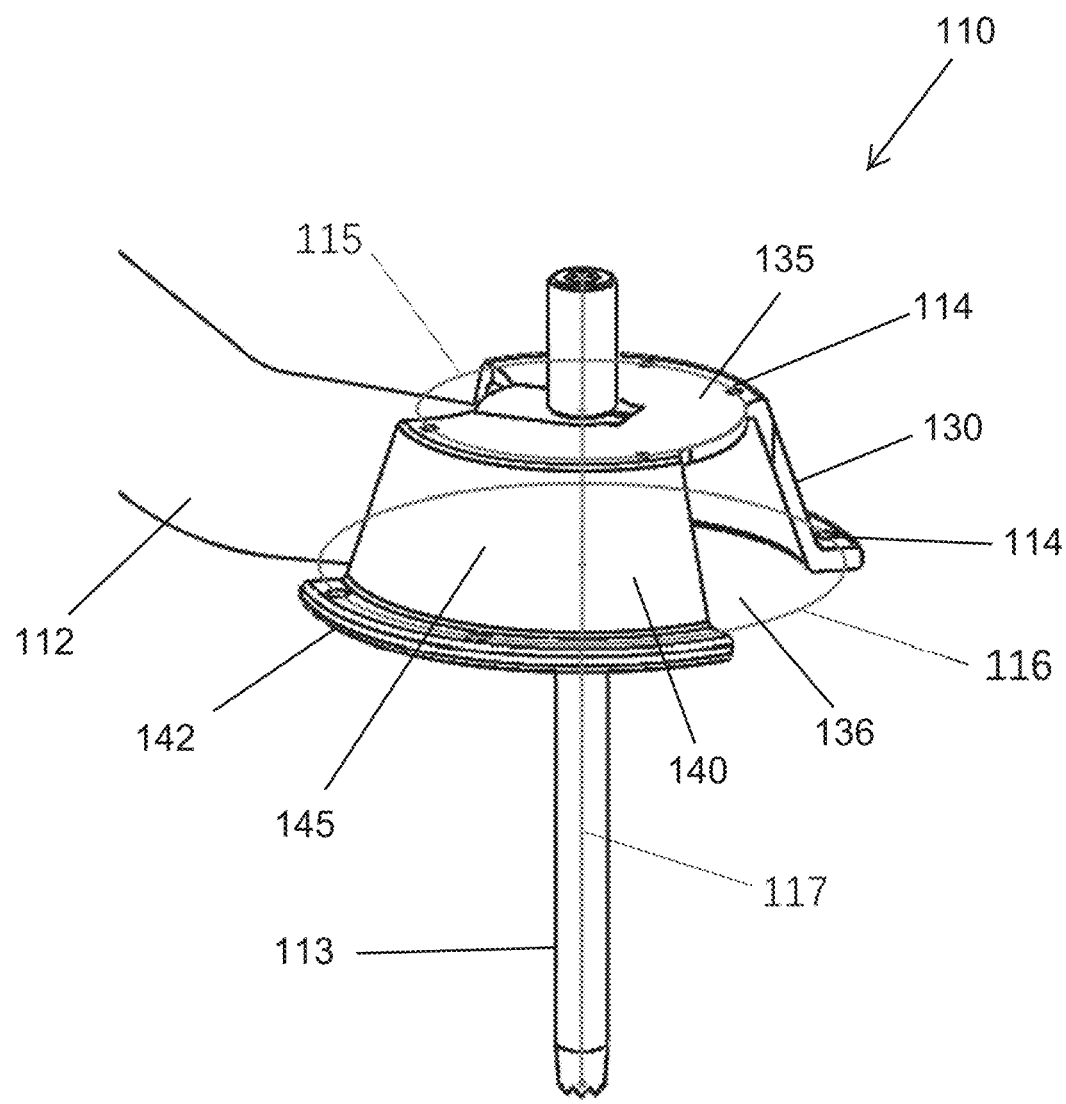
FIG. 7 is a perspective view of the end-effector of FIG. 4 showing the relationship between the drill guide and the beads of the end effector.

The registration device 130 has a proximal end 131, a distal end 132, an upper surface 133, and a lower surface 134, and generally comprises a rigid base 140 and beads 114. The base 140 comprises an inner portion 141, an outer portion 142, and a medial connecting wall or walls 145. As can be seen in FIGS. 5 and 7, the inner portion 141 is preferably planar and retains beads 114 in a first plane 135, while outer portion 142 is likewise preferably planar and other retains beads 114 in a second plane 136. Extending between the inner portion 141 and outer portion 142 are one or more medial connecting wall portions 145 which extend between and connect the inner portion 141 and the outer portion 142. In the illustrated embodiment, the medial connecting wall 145 is formed from two portions, a right side wall portion 146 and a left side wall portion 147, and the outer portion 142 is likewise formed in right side and left side portions. The medial connecting wall 145 is preferably frustoconical in shape, and extends inwardly from the outer portion 142 to the inner portion 141.

Figure 6:
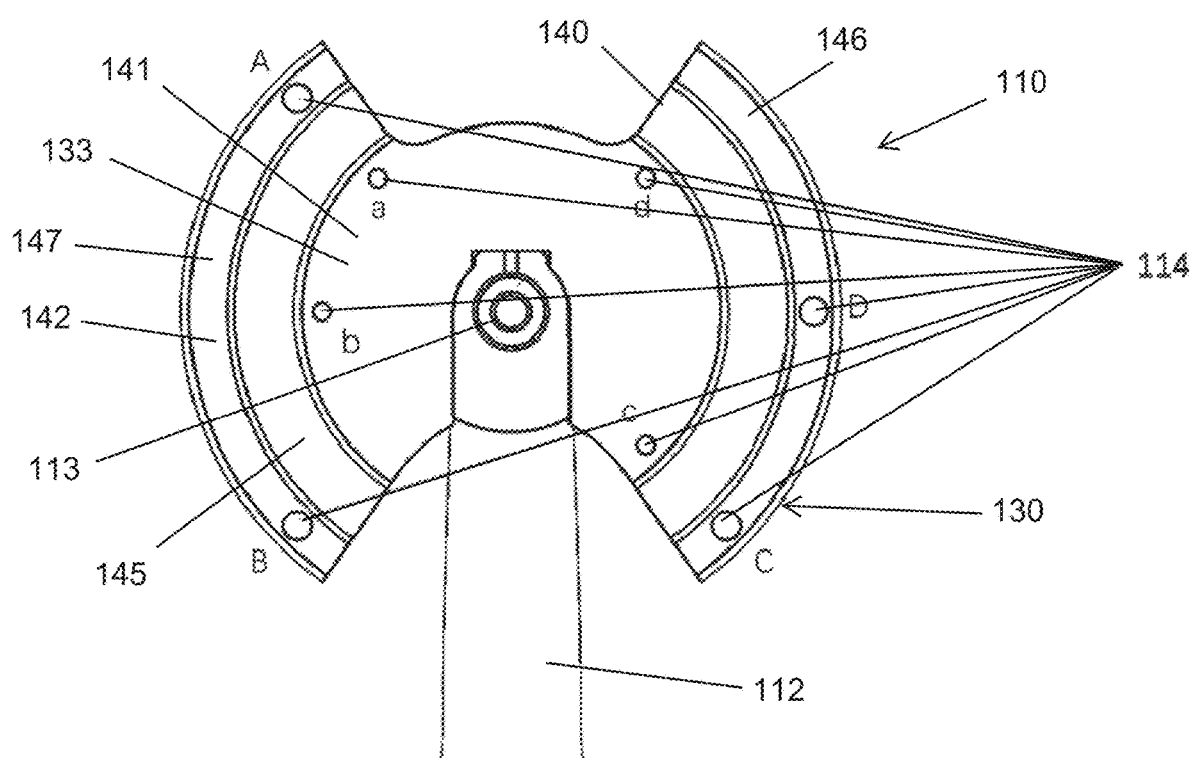
FIG. 6 a top plan view of the end-effector of FIG. 4 and the beads imbedded in the base of the end-effector.

FIG. 6 illustrates the configuration of the embedded beads 114 in the registration device 130. These beads 114 are used to accurately determine the intrinsic parameters of the C-arm of an X-ray machine and also the extrinsic parameters of the C-arm with respect to the robot arm 105. The beads 114 have two different diameters and are divided into two sets according to their diameters. The diameter of the larger diameter beads is larger than the diameter of the smaller diameter beads, preferably by at least 40 percent, and in this embodiment (as an example) the diameter of the larger beads is 1.5 times the diameter of the smaller beads. As seen in FIGS. 6 and 7, the centers of the larger diameter beads are in a second plane 136 which extends through the outer portion 142 of the base 140 and the centers of the smaller diameter beads are in a first, different plane 135 which extends through the inner portion 141 of the base 140. The first and second planes are preferably parallel. The centers of the larger beads make up the vertices of a convex polygon and the centers of the smaller beads make up the vertices of another convex polygon. Moreover, the polygons are inscribed polygons, which means their vertices locate on two different circles (115 and 116 in FIG. 7), respectively. The smaller beads, and the polygon which they form, preferably lie within the polygon formed by the larger beads, or vice versa, in order to better avoid occlusion between one of the small beads and one of the larger beads during imaging.

The use of different sizes of beads, as best seen in FIG. 6, is used to better distinguish the groups of beads in imaging. The larger beads can be divided in to two pairs, i.e. (A, C) and (B, D). The line between beads A and C and the line between beads B and D intersect at point E (not shown). The ratio of the distance between the center of a bead among the larger beads (A, B, C, D) and point E to the distance between the center of this bead to that of the other bead in the same pair is different between each bead among the larger beads (A, B, C, D). The smaller beads (a, b, c, d) can be also divided in to two pairs, i.e. (a, c) and (b, d). The line between beads a and c and the line between beads b and d intersect at point e (not shown). The ratio of the distance between the center of a bead among the smaller beads (a, b, c, d) and point e to the distance between the center of this bead to the center of the other bead in the same pair is different from the distances between each bead among the smaller beads (a, b, c, d). As shown in FIG. 7, the axis 117 of the drill guide coincides the centers of the circles where the first set and the second set of beads are located, and the axis of the drill guide are perpendicular to the planes where the first set and the second set of beads are located.

Robotic Surgical Processes

Figure 2:
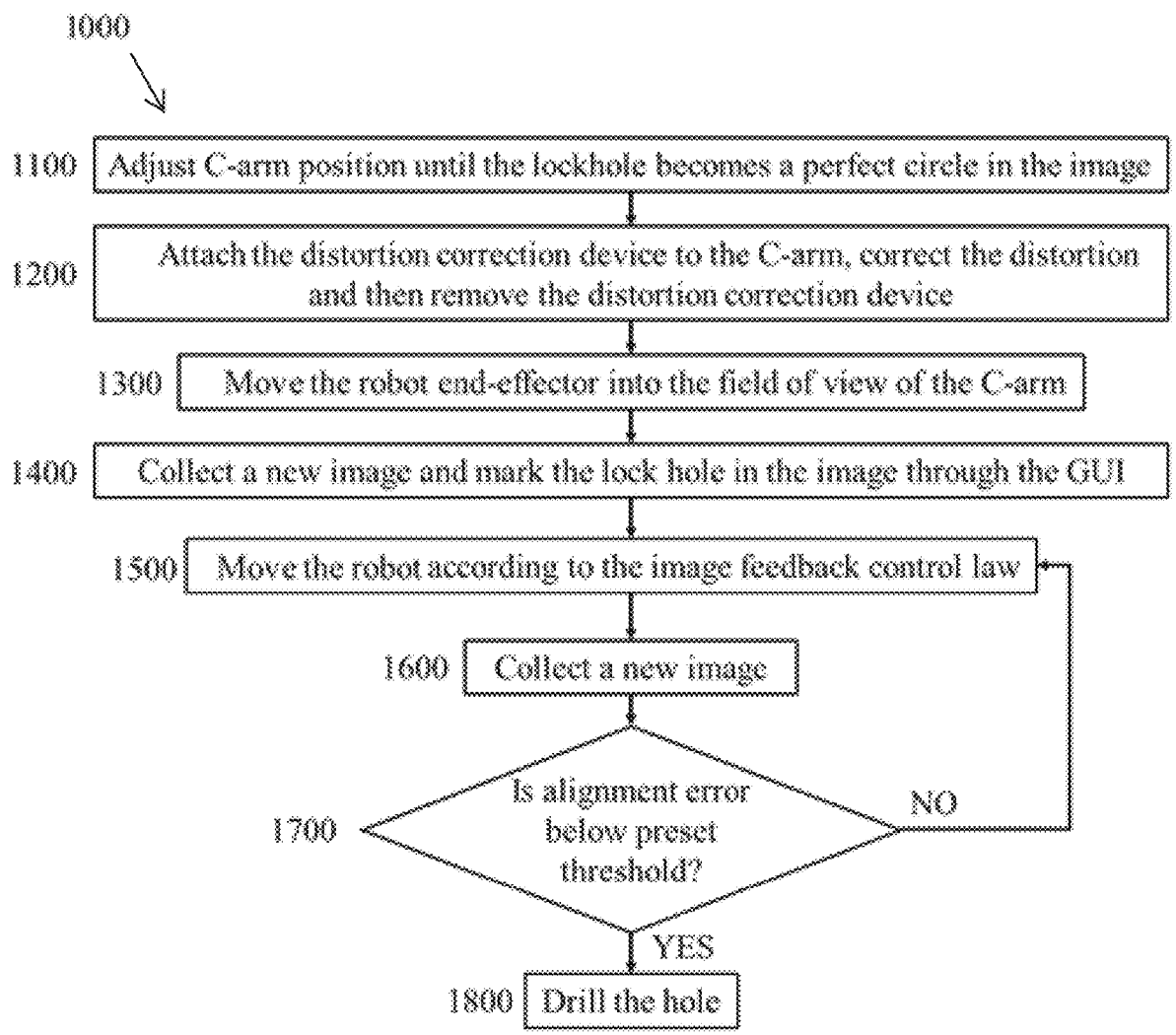
FIG. 2 is a diagram of steps of a robotic distal locking method.

FIG. 2 is a block diagram of exemplary image feedback control method 1000 for a distal locking operation based on the present 2D image-guided surgical robot system.

Figure 8:
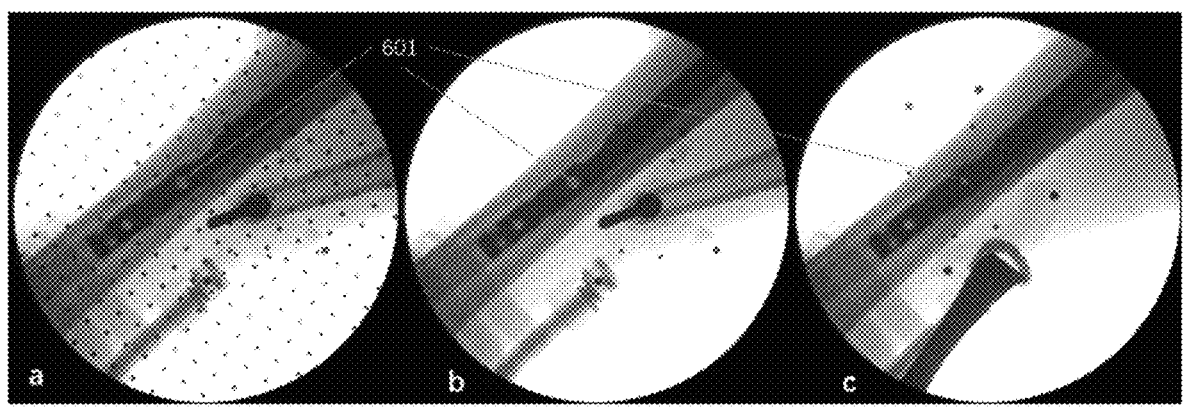
FIG. 8 shows a set of three photographs (labeled a, b, and c) of a surgical procedure being performed with the present system.

In step 1100, the position of the C-arm is adjusted by the surgeon such that the lockhole (which has a cylindrical bore) in the X-ray image is a perfect circle, as shown in FIG. 8.

In step 1200, the distortion correction device 210 is attached to the C-arm, then the distortion is corrected the distortion correction device 210 is removed.

In step 1300, the robot end-effector is moved into the field of view of the C-arm.

In step 1400, a new image is collected and the target lockhole is marked in the image through the GUI (graphical user interface). The position s of the marked lockhole 601 shown in FIG. 8 is represented with its pixel coordinate $s=[u v]^T$. As shown in FIG. 8(*b*), the lockhole and the beads on the robot end-effector clearly appear in the image.

In step 1500, the robot moves according to an image feedback control algorithm and then in step 1600 a new image is collected after the robot movement is finished.

The alignment error is calculated according to the image collected in step 1600. If the error is larger than a preset threshold, step 1500 and 1600 are repeated. Otherwise, proceed to step 1800.

In step 1800, the surgeon drills a guide wire through the drill guide. As the drill guide has been aligned to the lockhole (as shown in FIG. 8(*c*)), the guide wire will go through the lockhole, and then the surgeon can easily accomplish the distal locking by driving the locking screw through the guide hole drilled with the guide wire.

Figure 3:
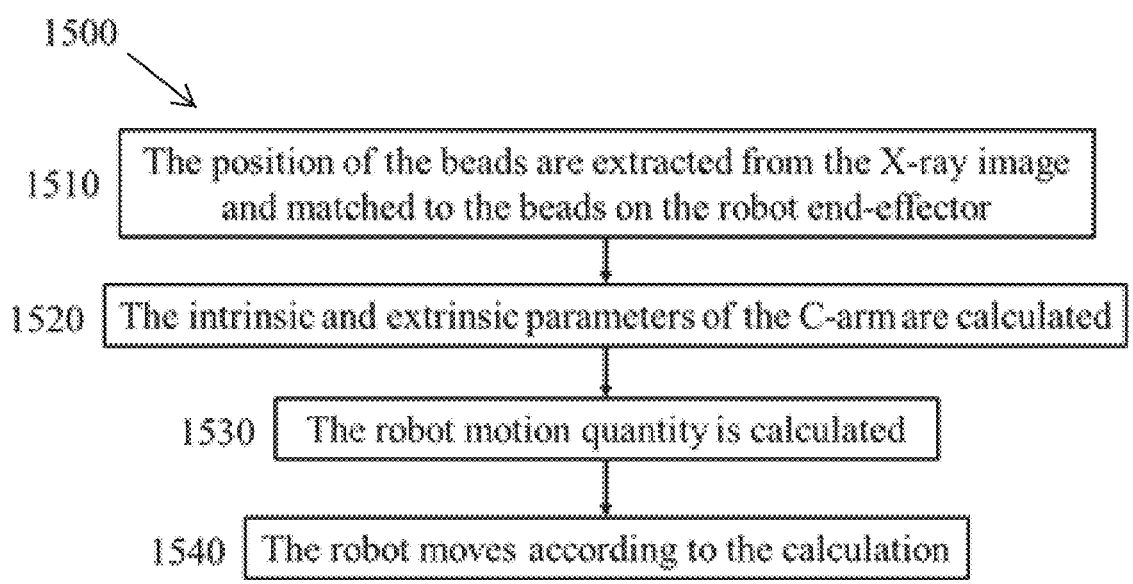
FIG. 3 is a diagram of steps of a robot control method.

FIG. 3 is a flowchart of an exemplary method 1500 for the robot control method in step 1500 of the above embodiment.

In step 1510, the position of the beads is extracted from the X-ray image and matched to the beads on the robot end-effector.

In step 1520, the intrinsic and extrinsic parameters of the C-arm is calculated according to the result of step 1510. The intrinsic parameters are represented using the 2-by-3 intrinsic matrix A, and the extrinsic parameters are represented with the translation vector $d_C^E$ and the rotation matrix $R_C^E$ from the C-arm coordinate frame to the end-effector coordinate frame.

In step 1530, the robot motion quantity is calculated according to the flowing substeps.

a), the position $X_{drill}^C$ and direction $n_{drill}^C$ of the drill guide in the C-arm coordinate frame is calculated. The position $X_{drill}^E$ and direction $n_{drill}^E$ of the drill guide in the robot end-effector coordinate frame is already known according to the CAD model of the end-effector. Thus $$x_{drill}^C = R_C^E x_{drill}^E + d_C^E$$

$$n_{drill}^C = R_C^E n_{drill}^E$$

b), the position $X_{hole}^C$ and direction $n_{hole}^C$ of the drilling path in the C-arm coordinate frame is calculated. The drilling path is the straight line going through the center of the target lockhole and also the focal point of the C-arm X-ray machine (origin of the C-arm coordinate frame). Thus $X_{hole}^C=0$ and $n_{hole}^C$ can be obtained by solving the flowing linear equation:

$$(A-[00s])n_{hole}^C=0$$

wherein s is the position of the lockhole in the X-ray image marked in step 1400.

c), the alignment error, including the position error $e_{pos}^C$ and direction error $e_{dir}^C$ is calculated as follows:

$$e_{pos}^C = \left(x_{hole}^C - x_{drill}^C\right) - \frac{\left(x_{hole}^C - x_{drill}^C\right) \Box n_{hole}^C}{\|x_{hole}^C - x_{drill}^C\|} n_{hole}^C$$

$$e_{dir}^C = \frac{n_{drill}^C \times n_{hole}^C}{\|n_{drill}^C \times n_{hole}^C\|} \cos^{-1}\left(\frac{n_{drill}^C \Box n_{hole}^C}{\|n_{drill}^C\|\|n_{hole}^C\|}\right)$$

d), the rotation matrix $R_E^R$ from the end-effector coordinate frame to the robot arm coordinate frame is obtained through robot arm kinematics (Corke, Peter. "Robotics, Vision and Control." Springer Tracts in Advanced Robotics 118(2017)).

e), the robot motion quantity defined in the robot arm coordinate frame, including the translational part $d^R$ and the rotational part $r^R$, is calculated according to:

$$d^R = \left(R_C^E R_E^R\right)^T e_{pos}^C$$

$$r^R = \left(R_C^E R_E^R\right)^T e_{dir}^C$$

In step 1540, the robot moves according to the motion quantity calculated above.

What is claimed is:

1. An end effector for a surgical robot arm comprising:
   (1) a connector arm having a proximal end and a distal end, wherein the proximal end is reversibly securable to the surgical robot;
   (2) a registration device secured to the distal end of the connector arm comprising:
      (a) a base made from an X-ray transparent material, the base comprising an inner portion, an outer portion, and a medial portion, wherein the medial portion extends between and connects the inner portion and the outer portion; and
      (b) at least 8 beads made from a material opaque to X-rays, wherein the beads comprise a first set of beads and a second set of beads, the first set of beads being attached to the inner portion of the base and the second set of beads being attached to the outer portion of the base, wherein the first set of beads has a first diameter and the second set of beads has a second diameter, and wherein the first diameter is different than the second diameter; and
   (3) a drill guide secured to the distal end of the connector arm,
   wherein centers of the first set of beads are in a first plane and are arranged to form vertices of a convex polygon in the first plane, and wherein centers of the second set of beads are in a second plane and are arranged to form vertices of a convex polygon in the second plane, the second plane being a different plane than the first plane, wherein the first and second planes are parallel,
   wherein the first set of beads can be grouped into pairs of beads, wherein lines extending between each of the pairs of beads cross at a first crossing point in the first plane, and wherein normalized distances between each of the first set of beads and the first crossing point are different,
   wherein the second set of beads can be grouped into pairs of beads, wherein lines extending between each of the pairs of beads cross at a second crossing point in the second plane, and wherein normalized distances between each of the second set of beads and the second crossing point are different,
   wherein the normalized distance is a ratio of the distance between a first bead of a pair of beads and a crossing point to the distance between the first bead and the second bead of the pair of beads, and
   wherein the drill guide extends along a longitudinal axis, and the longitudinal axis extends through the inner portion of the base at a right angle to the first and second planes.

2. The end effector for a surgical robot arm of claim 1, wherein the first set of beads has a diameter that is smaller than the diameter of the second set of beads.

3. The end effector for a surgical robot arm of claim 2, wherein the diameter of the second set of beads is between 0.4 and 1.5 times longer than the diameter of the first set of beads.

4. The end effector for a surgical robot arm of claim 1, wherein the second set of beads has a diameter that is smaller than the diameter of the first set of beads.

5. The end effector for a surgical robot arm of claim 4, wherein the diameter of the first set of beads is between 0.4 and 1.5 times longer than the diameter of the second set of beads.

6. The end effector for a surgical robot arm of claim 1, wherein the medial portion of the base is frustoconical in shape.

7. The end effector for a surgical robot arm of claim 1, wherein the medial portion of the base comprises a right side portion and a left side portion, and wherein the right side portion does not directly contact the left side portion.

8. A method for performing a distal locking operation with a surgical robot system, wherein the robot system comprises a robot arm with at least 3 translational degrees of freedom and 2 rotational degrees of freedom, the end-effector of claim 1 attached to the robot arm, 2D X-ray image acquisition device, an image distortion correction device and a display, comprising the steps of:
  a) adjusting the position and orientation of the 2D X-ray image acquisition device until a target lockhole appears in a first 2D X-ray image obtained by the X-ray image acquisition device;
  b) correcting image distortion by:
    mounting the image distortion correction device on the 2D X-ray image acquisition device of the robotic surgery system;
    collecting a second 2D X-ray image and then correcting the image distortion in the first 2D X-ray image; and
    unmounting the image distortion correction device from the 2D X-ray image acquisition device;
  c) moving the robot end-effector of claim 1 into the field of view of the 2D X-ray image acquisition device;
  d) collecting a third image, wherein the image depicts the robot end effector, and displaying it on the display, wherein the beads on the robot end-effector appear in the third image, and marking the target lockhole on the displayed image;
  e) moving the robot according to the position of the beads and the marked target lockhole in the 2D X-ray image;
  f) collecting a fourth image and calculating the alignment error between the drill guide and the lockhole;
  g) if the alignment error calculated in step f) is larger than a preset threshold, repeating step e) and step f); and
  h) drilling the guide hole for distal locking through the drill guide with a guide wire and then accomplishing the distal locking by screwing a locking screw along the guide hole.

* * * * *